(12) United States Patent
Gu et al.

(10) Patent No.: US 12,048,536 B2
(45) Date of Patent: Jul. 30, 2024

(54) OPTICAL DATA SENSING DEVICE OF BIOLOGICAL INFORMATION MEASURING DEVICE WHICH CAN IMPROVE MOTION ARTIFACT ISSUE

(71) Applicant: PixArt Imaging Inc., Hsin-Chu (TW)

(72) Inventors: Ren-Hau Gu, Hsin-Chu (TW); Hsiu-Ling Yeh, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 406 days.

(21) Appl. No.: 17/372,567

(22) Filed: Jul. 12, 2021

(65) Prior Publication Data
US 2023/0009213 A1    Jan. 12, 2023

(51) Int. Cl.
*A61B 5/1455*    (2006.01)
*A61B 5/00*    (2006.01)
*A61B 5/0205*    (2006.01)
*A61B 5/024*    (2006.01)

(52) U.S. Cl.
CPC ........ *A61B 5/14552* (2013.01); *A61B 5/0205* (2013.01); *A61B 5/02438* (2013.01); *A61B 5/7207* (2013.01); *A61B 2562/0238* (2013.01); *A61B 2562/185* (2013.01)

(58) Field of Classification Search
CPC .............. A61B 5/14552; A61B 5/0205; A61B 5/02438; A61B 5/7207; A61B 2562/0238; A61B 2562/185; A61B 5/02141; A61B 5/1123; A61B 2560/0204; A61B 5/02444; A61B 5/6801
See application file for complete search history.

(56) References Cited

U.S. PATENT DOCUMENTS

| | | | | |
|---|---|---|---|---|
| 6,845,256 B2 * | 1/2005 | Chin | .................... | A61B 5/6826 600/323 |
| 8,311,601 B2 * | 11/2012 | Besko | .................. | A61B 5/7207 600/323 |
| 10,813,578 B1 * | 10/2020 | Ben Ishay | .............. | A61B 5/681 |
| 2002/0007114 A1 * | 1/2002 | Elghazzawi | ......... | A61B 5/1455 600/323 |
| 2002/0035315 A1 * | 3/2002 | Ali | ........................ | A61B 5/746 600/323 |
| 2014/0127996 A1 * | 5/2014 | Park | ....................... | H04W 4/80 455/41.1 |
| 2014/0243633 A1 * | 8/2014 | Addison | ............ | A61B 5/14552 600/340 |
| 2017/0000350 A1 * | 1/2017 | Kwon | .................. | A61B 5/0059 |
| 2017/0315511 A1 * | 11/2017 | Shim | ...................... | A61B 5/721 |
| 2020/0085316 A1 * | 3/2020 | Zhou | .................. | A61B 5/02416 |

* cited by examiner

*Primary Examiner* — Eric F Winakur
*Assistant Examiner* — Abid A Mustansir
(74) *Attorney, Agent, or Firm* — Winston Hsu

(57) ABSTRACT

An optical data sensing device of a biological information measuring device, comprising: an optical sensor; a first light emitting device, configured to emit first light away from the optical sensor; and a first opaque isolation component, located between the optical sensor and the first light emitting device, configured to reduce the first light received by the optical sensor. The present invention also discloses an optical data sensing device comprising a plurality of light emitting devices with different emitting directions or wavelengths, to improve the accuracy of biological information measuring.

19 Claims, 9 Drawing Sheets

OPTICAL DATA SENSING DEVICE OF BIOLOGICAL INFORMATION MEASURING DEVICE WHICH CAN IMPROVE MOTION ARTIFACT ISSUE

BACKGROUND OF THE INVENTION

1. Field of the Invention

The present invention relates to an optical sensing device of a biological information measuring device, and particularly relates to an optical sensing device of a biological information measuring device which can improve motion artifact issue.

2. Description of the Prior Art

In recent years, a smart wearable electronic device such as a smart watch or a smart wristband has become more and more popular. Such smart wearable electronic device always has the function of biological information measuring (e.g. blood pressure, heart rate). The motion of the user (e.g., jogging, walking . . . ) may cause interference (or named motion artifact) to biological information measuring when the user wears the smart wearable electronic device. However, a conventional smart wearable electronic device has no proper mechanism for improving the motion artifact issue.

SUMMARY OF THE INVENTION

Therefore, one objective of the present invention is to provide an optical data sensing device of a biological information measuring device which can prevent the optical sensor from receiving non-necessary light.

Another objective of the present invention is to provide an optical data sensing device of a biological information measuring device which can improve an accuracy of biological information measuring.

One embodiment of the present invention discloses an optical data sensing device of a biological information measuring device, comprising: an optical sensor; a first light emitting device, configured to emit first light away from the optical sensor; and a first opaque isolation component, located between the optical sensor and the first light emitting device, configured to reduce the first light received by the optical sensor.

Another embodiment of the present invention discloses an optical data sensing device of a biological information measuring device, comprising: an optical sensor; a first light emitting device, configured to emit first light in a first direction; a second light emitting device, configured to emit second light in a second direction different from the first direction; and an first opaque isolation component, located between the optical sensor and the first light emitting device, and between the optical sensor and the second light emitting device, configured to reduce the first light and the second light received by the optical sensor.

In view of above-mentioned embodiments, the non-accuracy of biological information measuring caused by the motion artifact can be improved, since the optical sensor can be prevented from receiving non-necessary-light. Also, an accuracy of the biological information measuring can be further increased due to the application of light with different emitting directions or light with different wave lengths.

These and other objectives of the present invention will no doubt become obvious to those of ordinary skill in the art after reading the following detailed description of the preferred embodiment that is illustrated in the various figures and drawings.

DETAILED DESCRIPTION

Several embodiments are provided to explain the concept of the present invention. Please note, the term "first", "second" . . . are only for defining different steps or components, but do not mean any sequence thereof. For example, a first device and a second device are devices having the same structures but are different devices.

Figure 1:
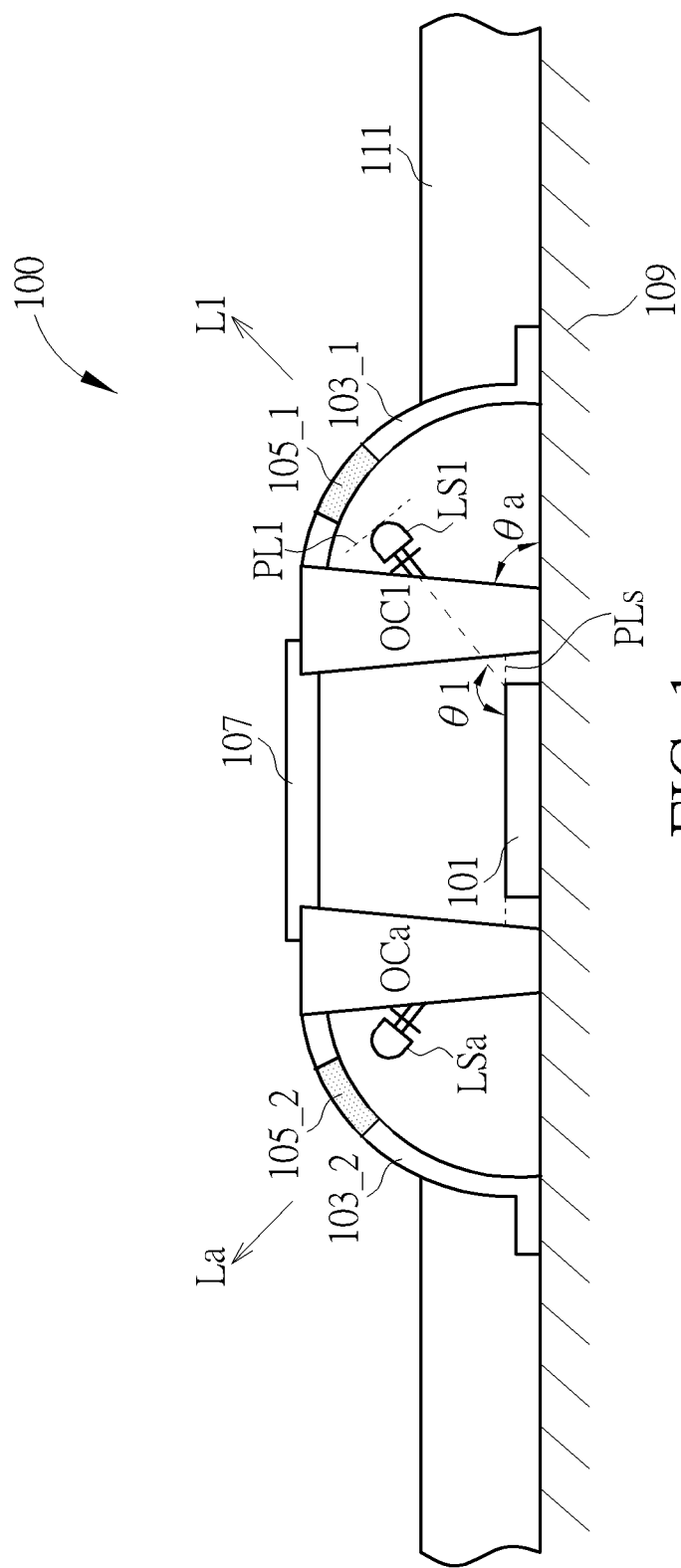
FIG. 1 is a schematic diagram illustrating an optical data sensing device according to one embodiment of the present invention.

FIG. 1 is a schematic diagram illustrating an optical data sensing device 100 according to one embodiment of the present invention. The optical data sensing device 100 can be applied but not limited to a biological information measuring device, which can measure biological information such as heart rate, blood pressure or oxygen saturation. In following embodiments, the biological information measuring device is a smart watch. However, the biological information measuring device can be any other kind of electronic device.

As illustrated in FIG. 1, the optical data sensing device 100 comprises an optical sensor 101 (e.g., an image sensor), a cover 103_1, and a first light emitting device LS1. The first light emitting device LS1 emits first light L1 away from the optical sensor 101. Many mechanisms can be applied to reach the effect that "the first light emitting device LS1 emits first light L1 away from the optical sensor 101". For example, reach such function by the emitting direction of the first light L1, or reach such function by the structure of the cover 103_1. Detail descriptions of how to reach such function will be explained later.

The first opaque isolation component OC1 is located between the optical sensor 101 and the first light emitting device LS1, and is configured to reduce the first light L1 received by the optical sensor 101. It will be appreciated that the "first light L1" in the descriptions "the first light L1 received by the optical sensor 101" can mean the first light L1 directly from the first light emitting device L1, reflected light of the first light L1 directly from the first light emitting device L1, or scattering light of the first light L1 directly from the first light emitting device LS1. Further, in the embodiment of FIG. 1 and in other embodiments, the light emitting device has a light source. However, the light emitting device can comprise a light source and at least one lens, which determines an emitting direction/range (direction or range) of the light from the light source. In such embodiment, the light source emits initial light and the lens is configured to refract/expand (direction or range) the initial light to generate the first light L1. The emitting direction of the first light L1 can be changed via changing the structure or the first light emitting device LS1.

In one embodiment, the first opaque isolation component OC1 completely blocks light from passing through. In another embodiment, light can partially penetrate the first opaque isolation component OC1. By this way, the first opaque isolation component OC1 can reduce the first light L1 received by the optical sensor 101.

In one embodiment, the first opaque isolation component OC1 is configured to define the emitting direction of the first light L1 such that an angle θ1 between an emitting direction of the first light L1 and a sensing surface of the optical sensor 101 is larger than 90°. Also, in another embodiment, an angle θa between a surface of the first opaque isolation component OC1 which faces the first light emitting device LS1 is smaller than 90°. More specifically, the angle θ1 faces the sensor cover 107.

The cover 103_1 covers the first light emitting device LS1. The cover 103_1 comprises at least one transparent portion (only one transparent portion 105_1 is illustrated in FIG. 1), such that the first light L1 can be emitted away from the optical sensor 101 via the transparent portion 105_1. The emitting direction of the first light L1 can be changed via changing the location or the material of the transparent portion.

In view of the embodiment illustrated in FIG. 1, since the first light emitting device LS1 emits the first light L1 away from the optical sensor 101 and the first opaque isolation component OC1 reduces the first light L1 received by the optical sensor 101, the first light L1 can be prevented from entering the optical sensor 101 before entering skins of the user even if the user wearing the biological information measuring device has some strong motions, such as jogging or weight training. Therefore, the biological information measuring can be prevented from being interfered by motion artifact, since the biological information is measured based on the first light L1 received by the optical sensor 101.

The optical data sensing device 100 is not limited to comprise only one light emitting device and only one opaque isolation component. For example, in the embodiment illustrated in FIG. 1, the optical data sensing device 100 further comprises an extra light emitting device LSa, an extra opaque isolation component OCa and a cover 105_2. Please the term "extra" here is only used for distinguishing form the term "first", and does not mean any limitation. The relations between the extra light emitting device LSa, the extra opaque isolation component OCa and the cover 105_2 are the same as which between the first light emitting device LS1, the first opaque isolation component OC1 and the cover 105_2. Also, the functions of the extra opaque isolation component OCa and the cover 105_2 are the same as which of the first opaque isolation component OC1 and the cover 105_1. Therefore, detail descriptions of the extra light emitting device LSa, the extra opaque isolation component OCa and the cover 105_2 are omitted for brevity here. Please note the emitting directions of first light L1 form the first light emitting device LS1 and extra light La from the extra light emitting device LSa can be identical or different.

It will be appreciated that the optical data sensing device provided by the present invention can have more than two opaque isolation components and more than two light emitting devices. In one embodiment, the first opaque isolation component OC1 and the extra opaque isolation component OCa are pillars having widths gradually decrease from top to bottom, but not limited.

In one embodiment, the first light emitting device LS1 and the extra light emitting device LSa are located symmetrically with the optical sensor 101. Also, in another embodiment, a distance between the optical sensor 101 and the first light emitting device LS1 is larger than or smaller than a distance between the optical sensor 101 and the extra light emitting device LSa.

The distances between the first light emitting device LS1/the extra light emitting device LSa and the optical sensor 101, and the distances between the first light emitting device LS1/the extra light emitting device LSa and the first opaque isolation component OC1/the extra opaque isolation component OCa may cause different effects to different motions. For example, smaller distances between the first light emitting device LS1/the extra light emitting device LSa and the first opaque isolation component OC1/the extra opaque isolation component OCa may cause better isolation if the user has a strong motion. On the opposite, larger distances between the first light emitting device LS1/the extra light emitting device LSa and the first opaque isolation component OC1/the extra opaque isolation component OCa may cause better isolation if the user has a weak motion.

In one embodiment, the optical data sensing device 100 further comprises a sensor cover 107 to cover the optical sensor 101. The sensor cover 107 can be a cover independent from the covers 105_1, 105_2. Also, the sensor cover 107, and the covers 105_1, 105_2 can be integrated to a single cover.

In one embodiment, the optical data sensing device 100 is provided at a substrate 109. Also, a projection image of the first light emitting device LS1 to the substrate 109 is not overlapped with a projection image of the optical sensor 101 to the substrate 109. In one embodiment, the substrate 109 is inside the biological information measuring device and can comprise at least one component of the biological information measuring device. In another embodiment, the substrate 109 is inside the biological information measuring device and is independent from components of the biological information measuring device.

Figure 2:
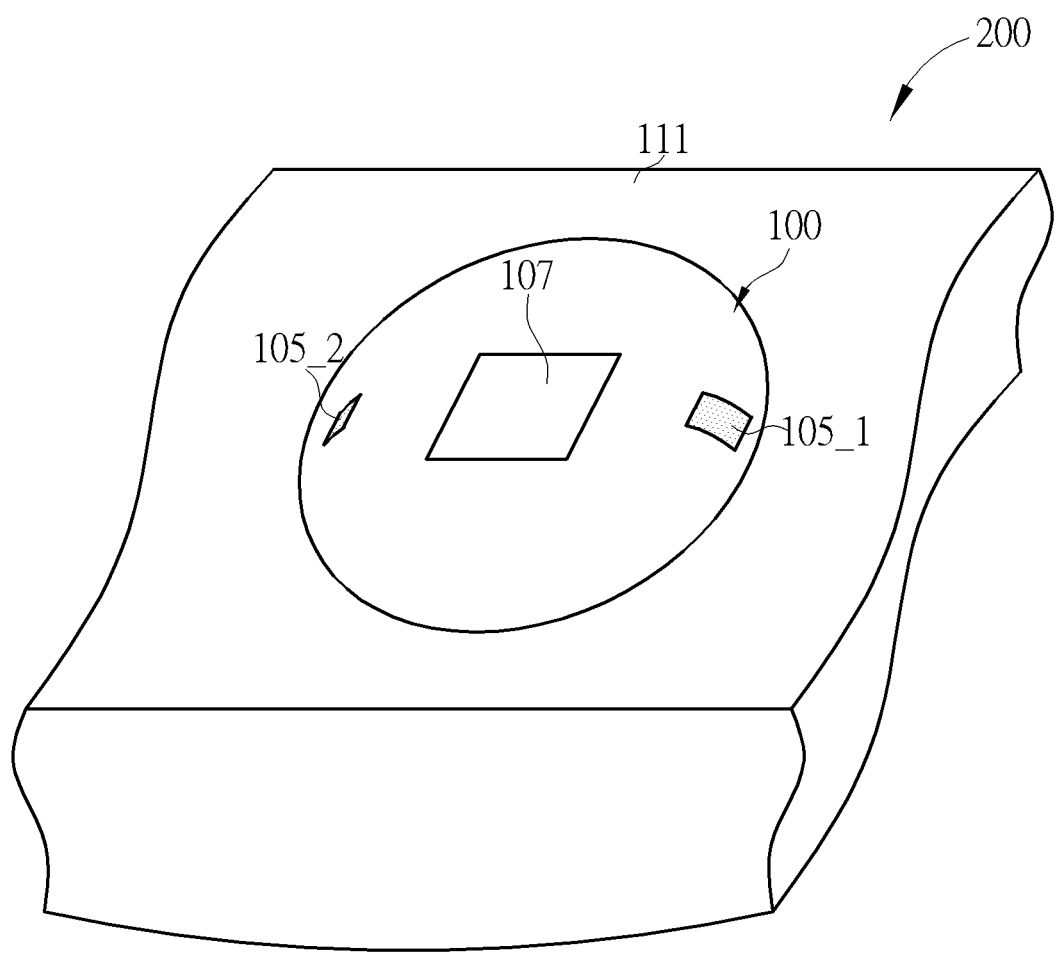
FIG. 2 is a schematic diagram illustrating an optical data sensing device in FIG. 1 from another view, according to one embodiment of the present invention.

In one embodiment, the covers 103_1 and 103_2 protrude from a surface 111 of the biological information measuring device. FIG. 2 is a schematic diagram illustrating an optical data sensing device in FIG. 1 from another view, according to one embodiment of the present invention. Please refer to FIG. 1 and FIG. 2 to understand the concepts of the present invention for more clarity. As illustrated in FIG. 2, the surface 111 is a back surface of a biological information measuring device 200 (e.g., a smart watch). Also, as illustrated in FIG. 2, the optical data sensing device 100 protrudes from the surface 111, such that the transparent portions 105_1, 1052 expose at the surface 111 and the from the light emitting devices inside the biological information measuring device 200 can be emitted outward via the transparent portions 105_1, 105_2.

Further, in FIG. 1, a plane PL1 from which the first light L1 is emitted outward and a plane PLs by which the optical sensor 101 receives light are different planes. In one embodiment, the plane PL1 is parallel a tangent plane of a portion of the transparent portion 105_1 from which the first light L1 is emitted outward, or the plane PL1 is a surface of the transparent portion 105_1 from which the first light L1 is emitted outward. Additionally, in one embodiment, the plane PLs is a sensing surface of the optical sensor 101, which is applied for receiving light.

Besides, in one embodiment, a color filter is provided on a surface of the transparent portion 105_1 from which the first light is emitted outward, or provided on the sensing surface of the optical sensor 101.

The color filter can define an angle range which light with a specific wavelength can pass. For example, the color filter can define an passable angle range which the light with a first wavelength can pass to be 30°-50°, and the color filter can define a passable angle range which the light with a second wavelength can pass to be 20°-60°. That is, for the color filter, the passable angle range for light with a first wavelength is smaller than the passable angle range for light with a second wavelength. Therefore, the color filter can be provided to limit an angle range that the optical sensor 101 can receive light. By this way, some reflected light which are from skins and may cause noise can be prevented from directly entering the optical sensor 101.

Figure 3:
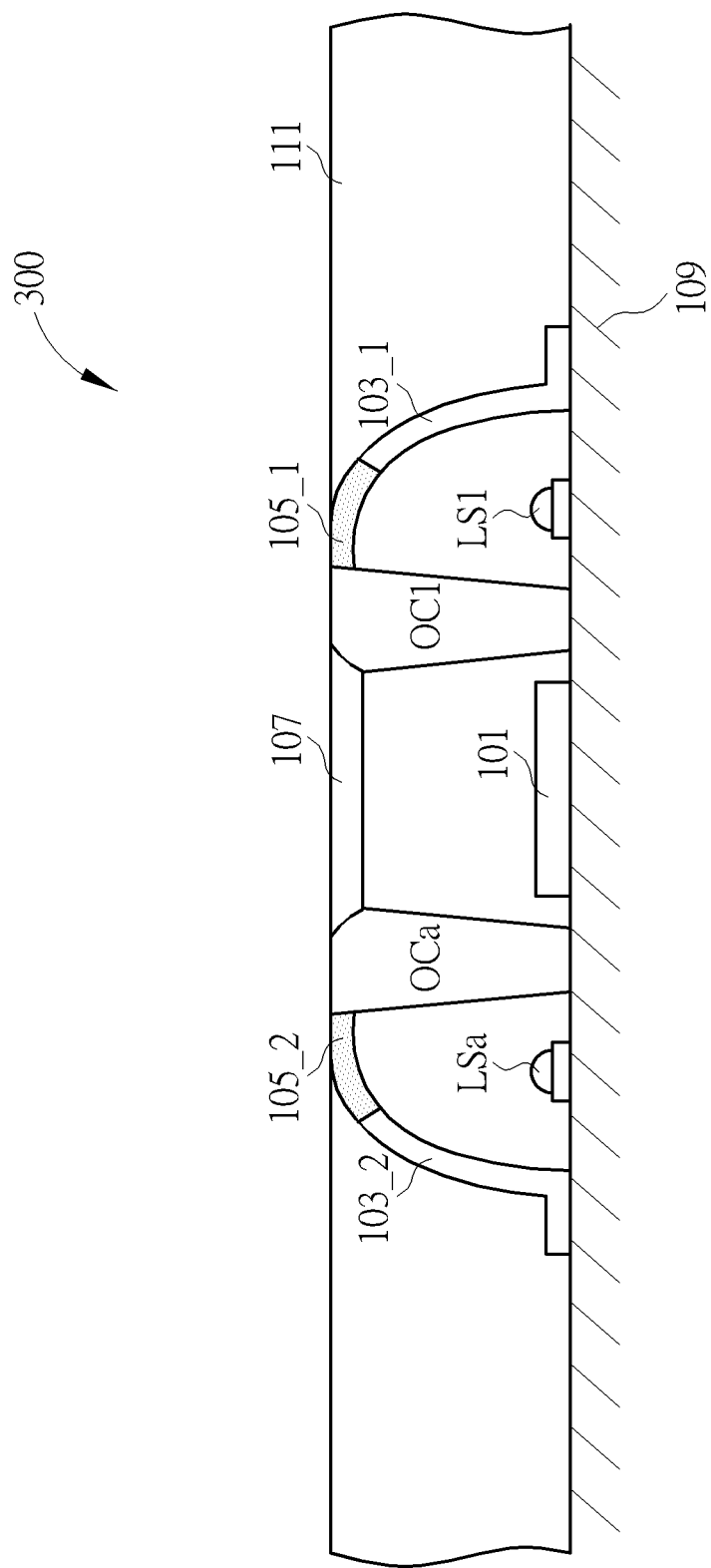
FIG. 3 is a schematic diagram illustrating an optical data sensing device according to another embodiment of the present invention.
Figure 4:
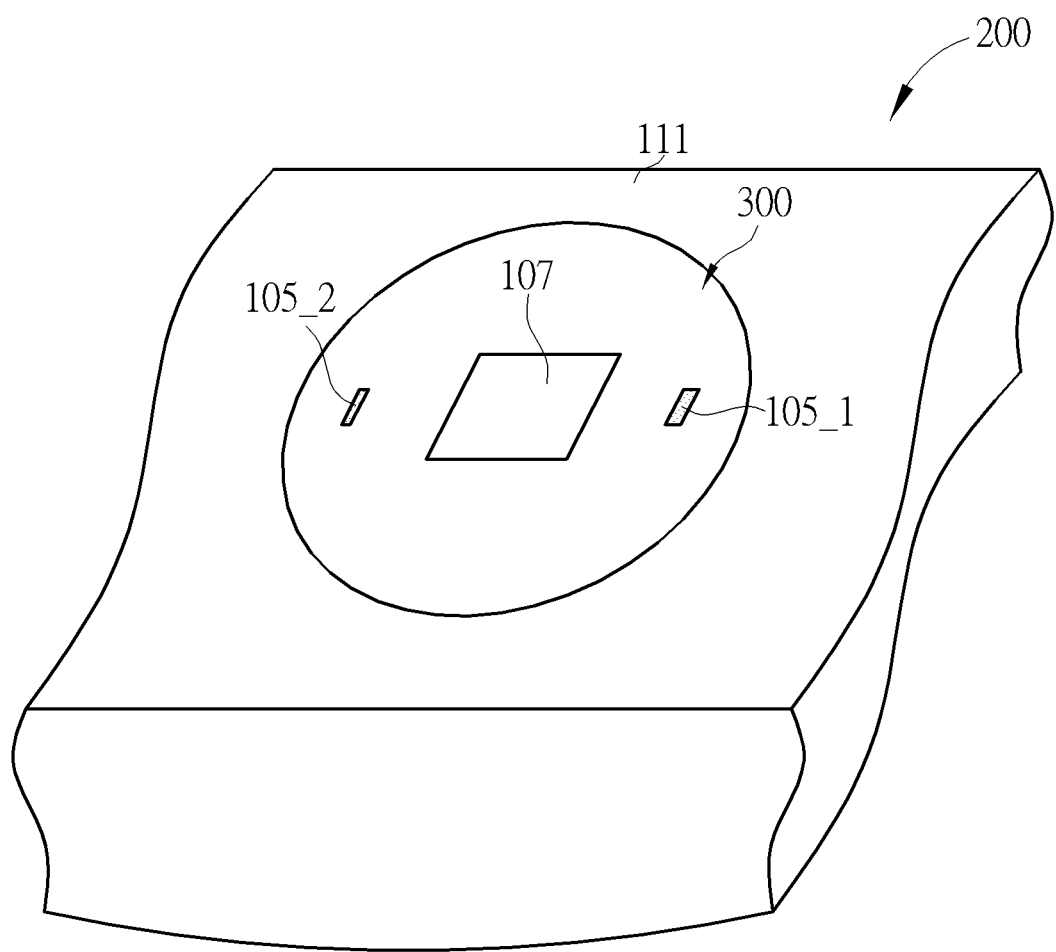
FIG. 4 is a schematic diagram illustrating an optical data sensing device in FIG. 3 from another view, according to one embodiment of the present invention.

However, the optical data sensing device 100 is not limited to protrude from the surface 111. FIG. 3 is a schematic diagram illustrating an optical data sensing device according to another embodiment of the present invention. FIG. 4 is a schematic diagram illustrating an optical data sensing device in FIG. 3 from another view, according to one embodiment of the present invention. Please refer to FIG. 3 and FIG. 4 to understand the concepts of the present invention for more clarity. As illustrated in FIG. 3 and FIG. 4, the optical data sensing device 300 is located in the biological information measuring device 200 and the transparent portions 105_1, 105_2 still expose at the surface 111. By this way, the light from the light emitting devices inside the biological information measuring device 200 can be emitted outward via the transparent portions 105_1, 105_2.

In the embodiment of FIG. 1, the emitting directions of the first light L1, extra light La are non-perpendicular with the surface 111. Also, in the embodiment of FIG. 3, the light emitting direction of the first light L1, extra light La are perpendicular with the surface 111, since the optical data sensing device 300 is inside the biological information measuring device 200. However, the light emitting direction is not limited to the embodiments illustrated in FIG. 1 and FIG. 3. Also, the locations and/or the sizes of the transparent portions 105_1, 105_2 can be changed corresponding to emitting directions of light.

Figure 5:
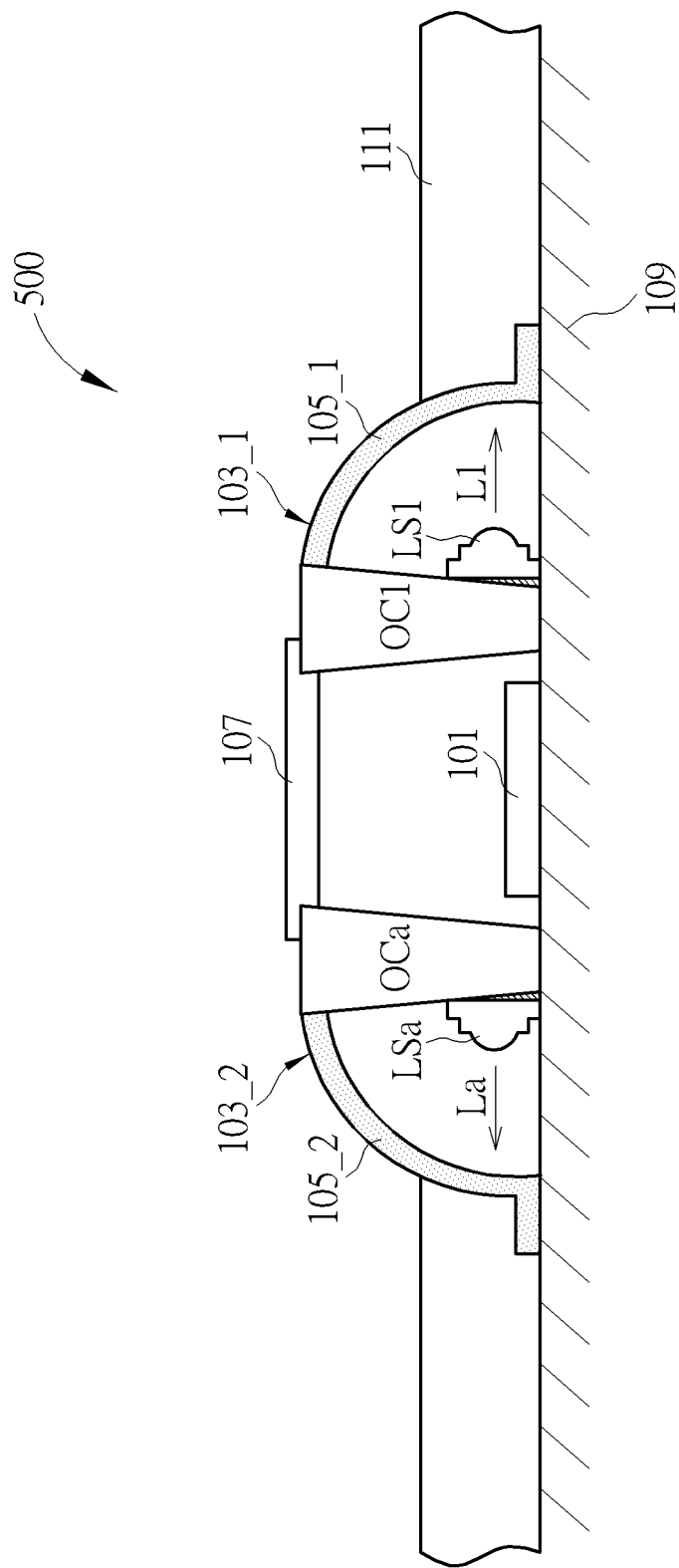
FIG. 5 and FIG. 6 are schematic diagrams illustrating optical data sensing devices according to different embodiments of the present invention.

The structures of the covers 103_1, 103_2 and the emitting directions of light are not limited to above-mentioned embodiments. FIG. 5 is a schematic diagram illustrating optical data sensing devices according to another embodiment of the present invention. As illustrated in FIG. 5, the emitting directions of the first light L1, the extra light La are perpendicular with the surface 111. Also, in the embodiment of FIG. 5, the transparent portions 105_1, 105_2 are light guide plates and occupy all of the covers 103_1, 103_2. Therefore, the structures of the covers 103_1, 103_2 and the emitting directions of light can be changed corresponding to different requirements. Such variations should also fall in the scope of the present invention.

Further, the shapes of the first opaque isolation component OC1 and the extra opaque isolation component OCa are not limited to the above-mentioned embodiments. Any shape which can prevent the light emitted by the light emitting devices from being received by the optical sensor should also fall in the scope of the present invention.

Figure 6:
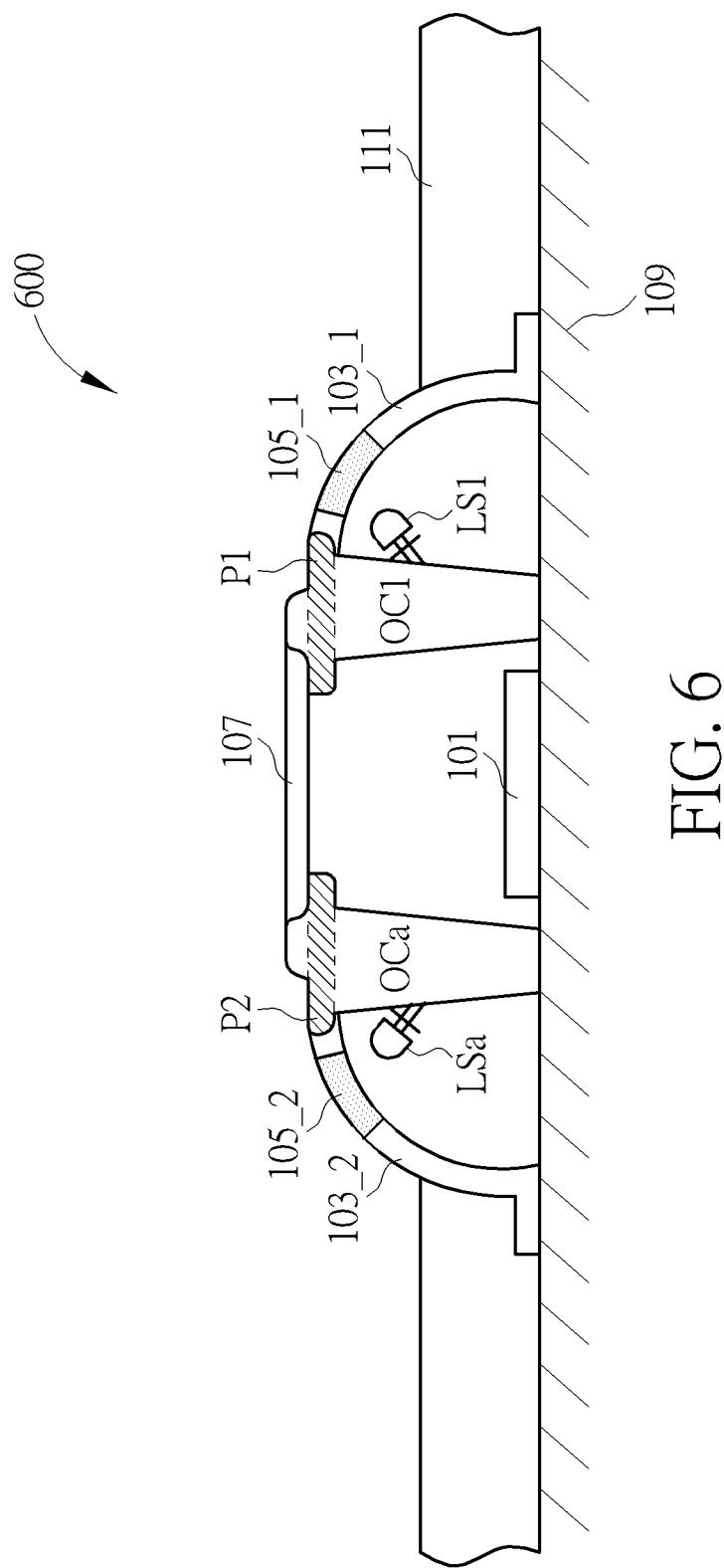

FIG. 6 is a schematic diagram illustrating optical data sensing device 600 according to another embodiment of the present invention. As illustrated in FIG. 6, the first opaque isolation component OC1 in the optical data sensing device 600 comprises at least one protruding part (only one protruding part P1 is illustrated in FIG. 6). The protruding part P1 is configured to partially or completely block the first light L1 received by the optical sensor 101 and to partially or completely block the first light L1 emitted from the first light emitting device LS1. Similarly, the extra opaque isolation component OCa in the optical data sensing device 600 comprises at least one protruding part (only one protruding part P2 is illustrated in FIG. 6). The protruding parts P2 is configured to partially or completely block the extra light La received by the optical sensor 101 and to partially or completely block the extra light La emitted from the extra light emitting device LSa. Please note, although the embodiment illustrated in FIG. 6 applies the embodiment illustrated in FIG. 1, the light emitting devices LS1, LSa illustrated in FIG. 6 can have any other structure or location.

In one embodiment, the protruding parts P1 and P2 are respectively located on the top of the first opaque isolation component OC1. Also, the protruding part which faces the light emitting device (e.g., the protruding part P1) protrudes from a side of the first opaque isolation component OC1. The extra opaque isolation component OCa can follow the same rule.

Figure 7:
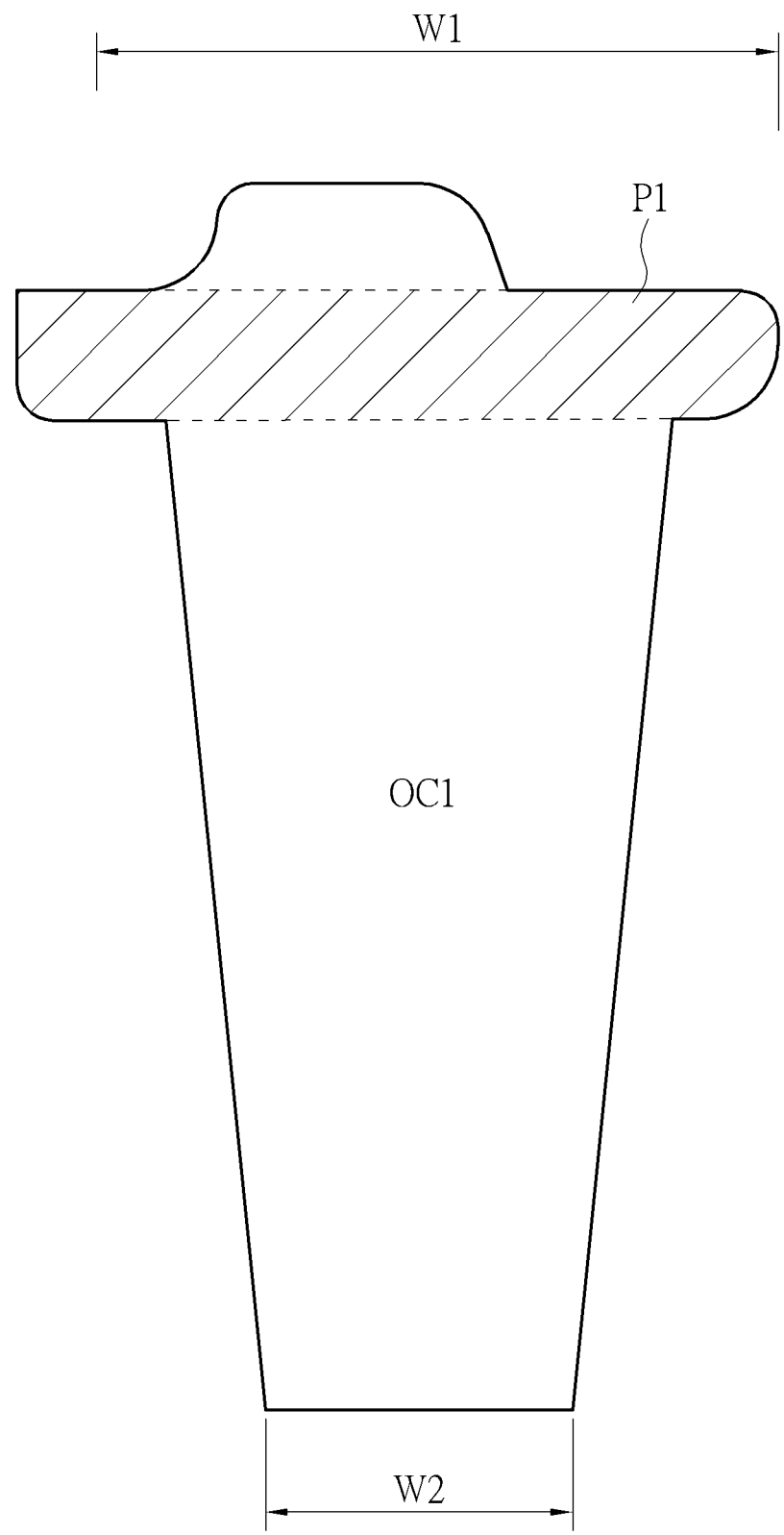
FIG. 7 is a schematic diagram illustrating the opaque isolation component according to one embodiment of the present invention.

FIG. 7 is a schematic diagram illustrating the opaque isolation component according to one embodiment of the present invention. As illustrated in FIG. 7, a width W1 of the protruding part P1 is wider than a narrowest width W2 of the first opaque isolation component OC1. The extra opaque isolation component OCa also follows such rule.

In above-mentioned embodiments, the first opaque isolation component OC1 and the extra opaque isolation component OCa are respectively between only one optical sensor 101. However, the first opaque isolation component OC1 and the extra opaque isolation component OCa can respectively between more than one optical sensor 101.

Figure 8:
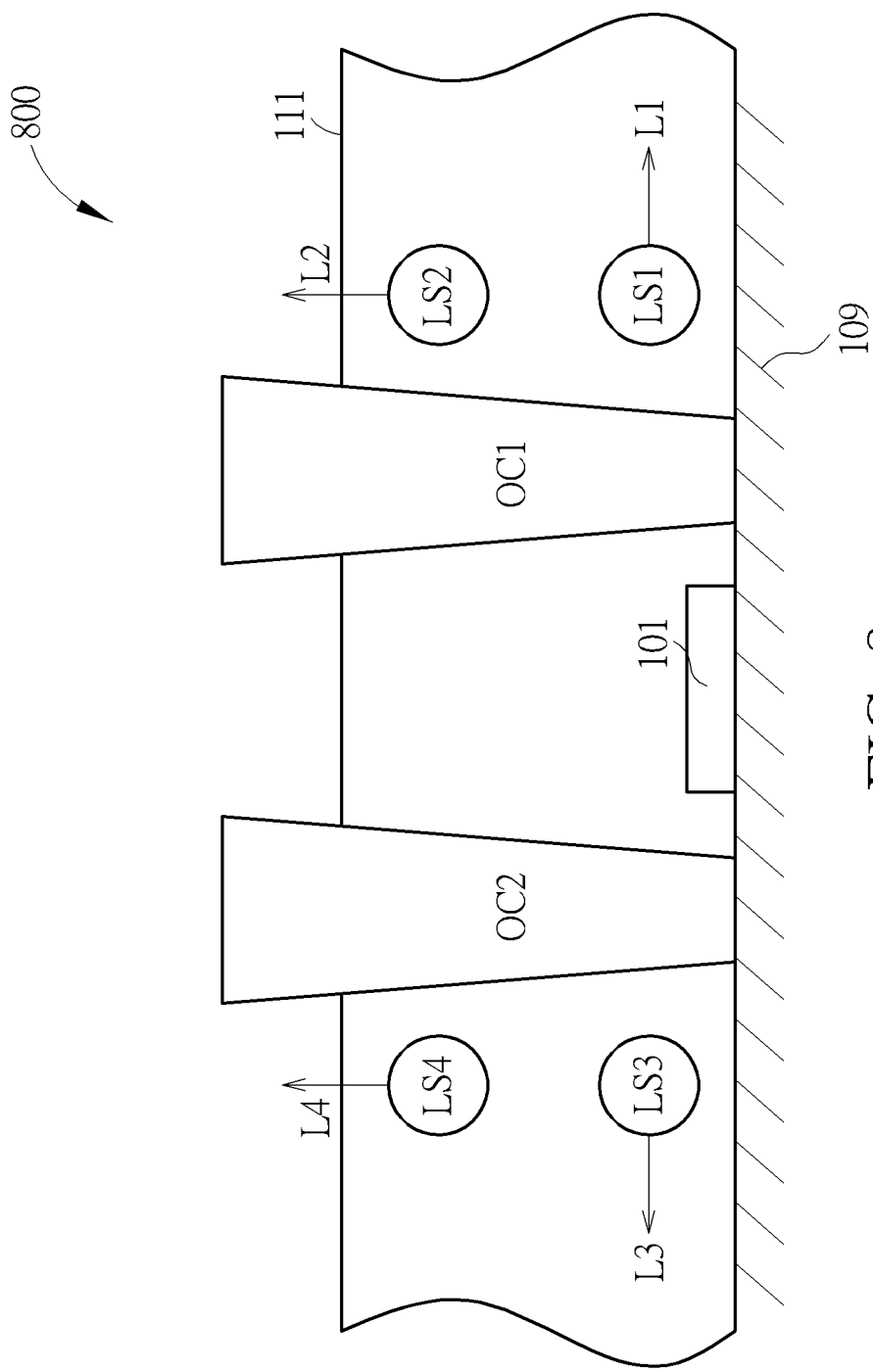
FIG. 8 and FIG. 9 are schematic diagrams illustrating optical data sensing devices comprising light emitting devices emitting light in different directions, according to embodiments of the present invention.
Figure 9:
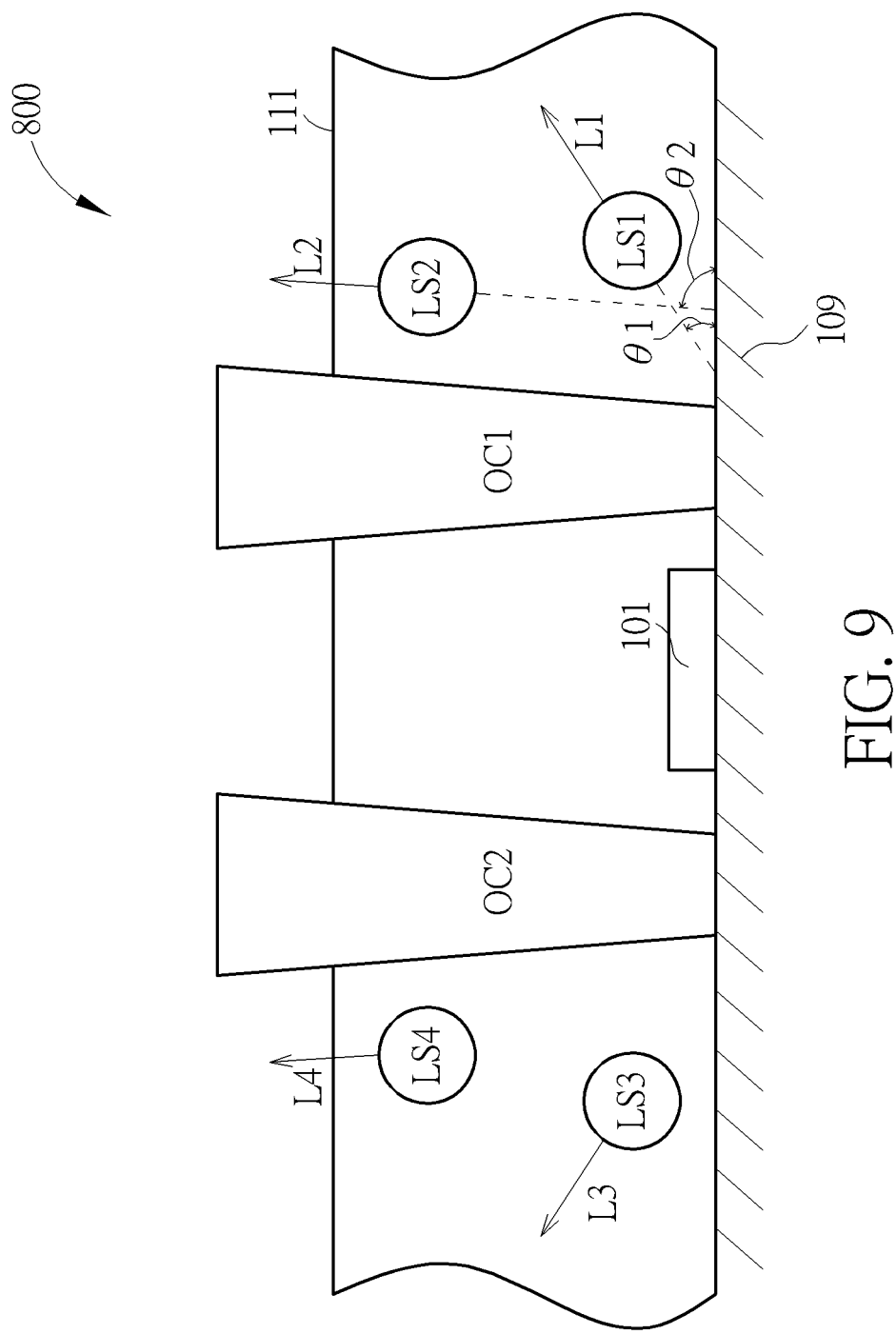

FIG. 8 and FIG. 9 are schematic diagrams illustrating optical data sensing devices comprising light emitting devices emitting light in different directions, according to embodiments of the present invention. Please note, for the convenience of explaining, some components such as covers 103_1 and 103_5 are not illustrated in FIG. 8 and FIG. 9. The optical data sensing device 800 comprises an optical sensor 101, a first light emitting device LS1, a second light emitting device LS2 and a first opaque isolation component OC1. The first light emitting device LS1 is configured to emit first light L1 in a first direction and the second light emitting device LS2 is configured to emit second light L2 in a second direction different from the first direction. In the embodiment of FIG. 8, the first direction is parallel with the substrate 109, and the second direction is perpendicular with the substrate 109.

The first opaque isolation component OC1 is located between the optical sensor 101 and the first light emitting device LS1 and is located between the optical sensor 101 and the second light emitting device LS2. The first opaque isolation component OC1 is configured to limit the first light L1 and the second light L2 received by the optical sensor 101.

It will be appreciated that the "first light L1, second light L2" in the descriptions "the first light L1, the second light L2 received by the optical sensor 101" can mean the first light L1, the second light L2 directly from the first light emitting device L1, the second light emitting device L2, reflected light of the first light L1, the second light L2 directly from the first light emitting device L1, the second light emitting device L2, or scattering light of the first light L1, the second light L2 directly from the first light emitting device L1, the second light emitting device L2.

In one embodiment, the first light L1 and the second light L2 are not simultaneously emitted. Also, the first light L1 and the second light L2 are respectively used for different functions. In one embodiment, the second light emitting device LS2 emits the second light L2 for computing a heart rate but the first light emitting device LS1 does not emit the first light L1, when the biological information measuring device comprising the optical data sensing device 800 computes the heart rate. Also, in one embodiment, the first light emitting device LS1 emits the first light L1 for computing oxygen saturation but the second light emitting device LS2 does not emit the second light L2, when the biological information measuring device comprising the optical data sensing device 800 computes the oxygen saturation.

In one embodiment, more than one optical sensor can be used. For example, two optical sensors having different color filters can be used. In such case, the first light L1 and the second light L2 can be simultaneously emitted.

Besides the above-mentioned biological information, the first light L1 and the second light L2 can be respectively used in modes with different noise levels. For example, the second light emitting device LS2 emits the second light L2 but the first light emitting device LS1 does not emit the first light L1, when the biological information measuring device comprising the optical data sensing device 800 operates in a low noise mode. In one embodiment, the low noise mode means a user wearing the biological information measuring device is not moving, or not jogging, or not running. For another example, the first light emitting device LS1 emits the first light L1 but the second light emitting device LS2 does not emit the second light L2, when the biological information measuring device comprising the optical data sensing device 800 operates in a high noise mode. In one embodiment, the high noise mode means a user wearing the biological information measuring device comprising the optical data sensing device 800 is moving, jogging or running. Since different motions may cause different light responses for light emitted in different emitting directions, the non-accuracy of biological information measuring caused by the motion artifact can be further improved by using light emitted in different emitting directions.

In another embodiment, the first light L1 and the second light L2 are still emitted non-simultaneously. However, the first light L1 and the second light L2 are used for the same function rather than different functions. For example, the biological information measuring device comprising the optical data sensing device 800 determines a wearing state thereof according to a difference between light amount of the first light L1 received by the optical sensor 101 and light amount of the second light L2 received by the optical sensor 101. Specifically, when the user does not wear the biological information measuring device comprising the optical data sensing device 800, a different between the light amount of the first light L1 received by the optical sensor 101 and light amount of the second light L2 is small, since neither the first light L1 nor the second light L2 is reflected by user's skin. Also, when the user does wears the biological information measuring device comprising the optical data sensing device 800, a different between the light amount of the first light L1 received by the optical sensor 101 and light amount of the second light L2 is large, since the first light L1 and the second light L2 are reflected by user's skin and the emitting directions of the first light L1 and the second light L2 are different.

Please refer to FIG. 8 again, in one embodiment, the optical data sensing device 800 is set at the above-mentioned substrate 109. A projection image of the first light emitting device LS1 to the substrate 109 is not overlapped with a projection image of the optical sensor 101 to the substrate 109, and a projection image of the second light emitting device LS2 to the substrate is not overlapped with the projection image of the optical sensor 101 to the substrate 109.

The optical data sensing device 800 can further comprise a third light emitting device LS3, a fourth light emitting device LS4 and a second opaque isolation component OC2. The third light emitting device LS3 is configured to emit third light L3 in a third direction. The fourth light emitting device LS4 is configured to emit fourth light L4 in a fourth direction different from the third direction. In one embodiment, the third direction is parallel with the above-mentioned substrate 109 and the fourth direction is perpendicular with the substrate 109.

The second opaque isolation component OC2 is located between the optical sensor 101 and the third light emitting device LS3, and located between the optical sensor 101 and the fourth light emitting device LS4, is configured to limit the third light L3 and the fourth light L4 received by the optical sensor. The relations and functions of the third light emitting device LS3, the fourth light emitting device LS4 and the second opaque isolation component OC2 can be the same as the first light emitting device LS1, the second light emitting device LS2 and the first opaque isolation component OC1, thus are omitted for brevity here.

In one embodiment, the first light L1, the third light L3 have different wavelengths, and the second light L2, the fourth light L4 have different wavelengths. For example, the first light L1 and the second light L2 are infrared light, but the third light L3 and the fourth light L4 are blue light. In such case, the first light L1, the third light L3 are selectively emitted in different modes, and the second light L2, the fourth light L4 are selectively emitted in different modes. For example, if the user wearing the biological information measuring device comprising the optical data sensing device 800 has whiter skins, the first light L1 and the second light L2 are used for measuring biological information of the user, and the third light L3 and the fourth light L4 are not used for measuring biological information of the user. Also, if the user wearing the biological information measuring device comprising the optical data sensing device 800 has darker skins, the third light L3 and the fourth light L4 are used for measuring biological information of the user, and the first light L1 and the second light L2 are not used for measuring biological information of the user.

In the embodiment of FIG. 8, the first direction is parallel with the substrate 109 and the second direction is perpendicular with the substrate 109. However, emitting directions of the first light L1 and the second light L2 are not limited to these examples. As shown in FIG. 9, the first light L1 is shifted counterclockwise and the second light L2 is shifted clockwise. The first light L1 and the second light L2 in FIG. 9 can still be used for functions the same as the functions of first light L1 and second light L2 in FIG. 8. In other words, as long as a smallest angle $\theta 1$ among angles between the first direction and the above-mentioned substrate 109 is smaller than a smallest angle $\theta 2$ among angles between the second direction and the substrate 109, the first light L1 and the second light L2 can in FIG. 9 be used for functions the same as the functions of first light L1 and second light L2 in FIG. 8.

In view of above-mentioned embodiments, the non-accuracy of biological information measuring caused by the motion artifact can be improved, since the optical sensor can be prevented from receiving non-necessary-light. Also, an accuracy of the biological information measuring can be further increased due to the application of light with different emitting directions or light with different wave lengths.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An optical data sensing device of a biological information measuring device, comprising:
   an optical sensor, provided at a surface of a substrate;
   a first light emitting device, configured to emit first light away from the optical sensor; and
   a first opaque isolation component, provided at the surface of the substrate, located between the optical sensor and the first light emitting device, configured to reduce the first light received by the optical sensor, wherein the first light emitting device is provided at a surface of the first opaque isolation component and does not touch the surface of the substrate.

2. The optical data sensing device of claim 1, further comprising:
   a cover, configured to cover the first light emitting device, wherein the cover comprises at least one transparent portion such that the first light can be emitted away from the optical sensor via the transparent portion.

3. The optical data sensing device of claim 2, wherein the cover protrudes from a surface of the biological information measuring device or is in the surface.

4. The optical data sensing device of claim 2, wherein an emitting direction of the first light is not perpendicular with the surface.

5. The optical data sensing device of claim 1, wherein the first light emitting device comprises:
   a light source, configured to emit initial light; and
   at least one lens, configured to refract the initial light to generate the first light.

6. The optical data sensing device of claim 1, further comprising:
   an extra light emitting device, configured to emit extra light away from the optical sensor, wherein the extra light emitting device is not overlapped with the optical sensor and the first light emitting device; and
   an extra opaque isolation component, located between the optical sensor and the extra light emitting device, configured to reduce the extra light received by the optical sensor.

7. The optical data sensing device of claim 1, wherein the first opaque isolation component comprises at least one protruding part, configured to block the first light received by the optical sensor and to block the first light emitted from the first light emitting device.

8. The optical data sensing device of claim 7, wherein a width of the protruding part is wider than a narrowest width of the first opaque isolation component.

9. The optical data sensing device of claim 1, wherein a plane from which the first light is emitted outward and a plane by which the optical sensor receives light are different planes.

10. The optical data sensing device of claim 1, wherein a color filter is provided on a surface of the transparent portion from which the first light is emitted outward, or provided on a sensing surface of the optical sensor, wherein the sensing surface of the optical sensor is configured to receive light.

11. An optical data sensing device of a biological information measuring device, comprising:
    an optical sensor;
    a first light emitting device, configured to emit first light in a first direction;
    a second light emitting device, configured to emit second light in a second direction different from the first direction; and
    a first opaque isolation component, located between the optical sensor and the first light emitting device, and between the optical sensor and the second light emitting device, configured to reduce the first light and the second light received by the optical sensor;
    wherein the first light and the second light are not simultaneously emitted;
    wherein the optical data sensing device is set at a substrate, wherein a smallest angle among angles between the first direction and the substrate is smaller than a smallest angle among angles between the second direction and the substrate;
    wherein the second light emitting device emits the second light but the first light emitting device does not emit the first light, when the biological information measuring device operates in a low noise mode.

12. The image sensing device of claim 11, wherein the second light emitting device emits the second light for computing a heart rate but the first light emitting device does not emit the first light, when the biological information measuring device computes the heart rate.

13. The optical data sensing device of claim 11, wherein the first light emitting device emits the first light for computing oxygen saturation but the second light emitting device does not emit the second light, when the biological information measuring device computes the oxygen saturation.

14. The optical data sensing device of claim 11, wherein the low noise mode means a user wearing the biological information measuring device is not moving or not jogging.

15. The optical data sensing device of claim 11, wherein the first light emitting device emits the first light but the second light emitting device does not emit the second light, when the biological information measuring device operates in a high noise mode.

16. The optical data sensing device of claim 15, wherein the high noise mode means a user wearing the biological information measuring device is moving or jogging.

17. The optical data sensing device of claim 11, further comprising:
    a third light emitting device, configured to emit third light in a third direction;
    a fourth light emitting device, configured to emit fourth light in a fourth direction different from the third direction; and
    a second opaque isolation component, located between the optical sensor and the third light emitting device and located between the optical sensor and the fourth light emitting device, configured to reduce the third light and the fourth light received by the optical sensor;

wherein the first light, the third light have different wavelengths, and the second light, the fourth light have different wavelengths;

wherein the first light, the third light are selectively emitted in different modes, and the second light, the fourth light are selectively emitted in different modes.

18. The optical data sensing device of claim 11, wherein the biological information measuring device determines a wearing state thereof according to a difference between light amount of the first light received by the optical sensor and light amount of the second light received by the optical sensor.

19. An optical data sensing device of a biological information measuring device, comprising:
an optical sensor;
a first light emitting device, configured to emit first light in a first direction;
a second light emitting device, configured to emit second light in a second direction different from the first direction; and
a first opaque isolation component, located between the optical sensor and the first light emitting device, and between the optical sensor and the second light emitting device, configured to reduce the first light and the second light received by the optical sensor;

wherein the first light and the second light are not simultaneously emitted;

wherein the optical data sensing device is set at a substrate, wherein a smallest angle among angles between the first direction and the substrate is smaller than a smallest angle among angles between the second direction and the substrate;

wherein the first light emitting device emits the first light but the second light emitting device does not emit the second light, when the biological information measuring device operates in a high noise mode.

* * * * *